US012714807B2

(12) United States Patent
Helmlinger et al.

(10) Patent No.: US 12,714,807 B2
(45) Date of Patent: Aug. 25, 2026

(54) INHALER AND EVALUATION UNIT THEREFOR

(71) Applicant: Aptar Radolfzell GmbH, Radolfzell (DE)

(72) Inventors: Michael Helmlinger, Radolfzell-Böhringen (DE); Marius Karge, Stockach (DE); Kevin Schmid, Constance (DE)

(73) Assignee: APTAR RADOLFZELL GMBH, Radolfzell (DE)

(*) Notice: Subject to any disclaimer, the term of this patent is extended or adjusted under 35 U.S.C. 154(b) by 1231 days.

(21) Appl. No.: 17/627,325

(22) PCT Filed: Aug. 4, 2020

(86) PCT No.: PCT/EP2020/071931
§ 371 (c)(1),
(2) Date: Jan. 14, 2022

(87) PCT Pub. No.: WO2021/032471
PCT Pub. Date: Feb. 25, 2021

(65) Prior Publication Data

US 2022/0273891 A1 Sep. 1, 2022

(30) Foreign Application Priority Data

Aug. 21, 2019 (EP) .................................... 19192926

(51) Int. Cl.
*A61M 15/00* (2006.01)

(52) U.S. Cl.
CPC ...... *A61M 15/0018* (2014.02); *A61M 15/009* (2013.01); *A61M 2205/332* (2013.01);
(Continued)

(58) Field of Classification Search
CPC .. A61M 11/08; A61M 15/00; A61M 15/0001; A61M 15/0018; A61M 15/009;
(Continued)

(56) References Cited

U.S. PATENT DOCUMENTS 6,550,324 B1 * 4/2003 Mayer .................. G01F 1/6986 73/204.14
6,958,691 B1 10/2005 Anderson et al.
(Continued)

FOREIGN PATENT DOCUMENTS

CA 3018628 A1 10/2017
EP 2221079 A1 8/2010
(Continued)

OTHER PUBLICATIONS

Japanese Office Action with English translation issued in corresponding Japanese Application No. 2021-576394 dated Jan. 27, 2023 (9 pages).

(Continued)

*Primary Examiner* — Douglas Y Sul
(74) *Attorney, Agent, or Firm* — FLYNN THIEL, P.C.

(57) ABSTRACT

An inhaler with an evaluation unit, a housing with a mouthpiece and a chamber with a container unit. Provided between the container unit and a chamber wall is an annular gap, through which air is sucked in and mixes with medium flowing through a discharge. The evaluation unit is mounted on the container unit and is pressed down together with a container of the container unit and detects air sucked through the annular gap. A measuring channel forms part of a first flow path for air flowing into the chamber from a surrounding area and a flow sensor detects the air flowing through the measuring channel. A second flow path is provided for air flowing into the chamber from a surround-
(Continued)

ing area, the flow resistance of which second path is equal to or lower than that of the first flow path.

25 Claims, 3 Drawing Sheets

(52) U.S. Cl.
CPC ............... *A61M 2205/3327* (2013.01); *A61M 2205/3334* (2013.01); *A61M 2205/3368* (2013.01); *A61M 2205/3584* (2013.01); *A61M 2205/3592* (2013.01); *A61M 2205/36* (2013.01); *A61M 2205/8206* (2013.01)

(58) Field of Classification Search
CPC ............ A61M 15/02; A61M 2016/003; A61M 2016/0033; A61M 2016/0021; A61M 2016/0018; A61M 2205/3334; A61M 2205/332; A61M 2205/3584; A61M 2206/10; A61B 5/087; A61B 5/0878
USPC .......................................... 73/201.11–204.27
See application file for complete search history.

(56) References Cited

U.S. PATENT DOCUMENTS

| | | | | |
|---|---|---|---|---|
| 8,215,299 | B2 * | 7/2012 | Wu | A61M 15/008 128/200.14 |
| 9,381,313 | B2 | 7/2016 | Bari | |
| 2004/0118200 | A1 * | 6/2004 | Hornung | G01F 5/00 73/202 |
| 2006/0118107 | A1 * | 6/2006 | King | A61M 15/0005 128/200.14 |
| 2006/0254581 | A1 * | 11/2006 | Genova | A61M 15/0065 128/200.23 |
| 2010/0166512 | A1 * | 7/2010 | Tanibuchi | C23C 16/36 427/255.15 |
| 2012/0012106 | A1 * | 1/2012 | Bari | A61M 15/008 128/200.23 |
| 2012/0080029 | A1 * | 4/2012 | Koerner | A61M 15/008 222/23 |
| 2013/0151162 | A1 | 6/2013 | Harris et al. | |
| 2013/0298907 | A1 * | 11/2013 | Zuyderhoudt | A61M 15/0065 128/203.12 |
| 2016/0144141 | A1 * | 5/2016 | Biswas | A61M 15/009 128/200.23 |
| 2017/0290527 | A1 * | 10/2017 | Morrison | A61B 5/4833 |
| 2019/0001085 | A1 * | 1/2019 | Cottenden | A61M 15/002 |
| 2019/0224426 | A1 * | 7/2019 | Farina | A61M 15/009 |
| 2021/0146070 | A1 * | 5/2021 | Consoli | A61M 15/008 |
| 2022/0273235 | A1 * | 9/2022 | Markey | A61M 15/007 |

FOREIGN PATENT DOCUMENTS

| | | | |
|---|---|---|---|
| JP | 2019506261 | A | 3/2019 |
| WO | 2017112400 | A1 | 6/2017 |
| WO | 2017205824 | A1 | 11/2017 |
| WO | 2018/138788 | A1 | 8/2018 |
| WO | 2018154407 | A1 | 8/2018 |
| WO | 2018200655 | A1 | 11/2018 |

OTHER PUBLICATIONS

Office Action issued in corresponding India Application No. 202217012839, dated Dec. 9, 2022 (5 pages).

International Search Report with English Translation issued in corresponding International Application No. PCT/EP2020/071931 date of mailing Oct. 1, 2020 (5 pages).

Written Opinion of International Searching Authority issued in corresponding International Application No. PCT/EP2020/071931 dated Oct. 1, 2020 (5 pages).

European Search Report issued in corresponding European Application No. 19 19 2926.4 with English translation of categories of cited documents, dated Mar. 10, 2020 (7 pages).

* cited by examiner

INHALER AND EVALUATION UNIT THEREFOR

FIELD OF THE INVENTION

The invention relates to an inhaler for dispensing an inhalable medium, in particular an atomized liquid. An inhaler is characterized by an evaluation unit which is mounted on a container of the inhaler. In addition to the inhaler with such an evaluation unit, the invention also relates to the evaluation unit as such.

An inhaler, which is provided with an evaluation unit, can be designed in particular as an MDI dispenser (metered dose inhaler). Such MDI dispensers are usually more or less L-shaped and have a vertically oriented main body, which includes a chamber for a container unit, and a mouthpiece which is connected to the lower end of the main body and is angled relative to the main body.

BACKGROUND OF THE INVENTION

The use of generic inhalers involves a user placing the mouthpiece between their lips and inhaling through the inhaler so that air is sucked in through the housing of the inhaler. The air usually flows into the housing through a gap between the container unit and a surrounding wall of the chamber. The flow resistance is low, so that no appreciable effort is needed to inhale. While breathing in, the user presses on the container unit from above and thereby causes atomized liquid to be discharged into the air stream, such that the inhaled air is mixed with droplets of the liquid and is inhaled by the user.

The desired medical effect of the inhalation depends to a considerable extent on the user complying with the intended parameters, that is inhaling strongly enough and causing the liquid to be discharged at the right time.

The prior art has included dispensers which monitor compliance with these parameters and, if necessary, give feedback to the user or, if necessary, also send data on the use of the dispenser and on the compliance with the parameters, in particular for evaluation by a physician.

Evaluation units are also already known which are placed on a container floor in order to be pressed down by the user, together with the container, in relation to the housing of the inhaler.

WO 2017/205824 A1 discloses an evaluation unit for an inhalation dispenser, having a pressure tube which leads from the annular gap of an inhaler, between the housing wall and the container, to a board on which a pressure sensor is provided. The pressure sensor is used to detect a pressure in the aforementioned annular gap.

US 2016/0144141 A1 discloses an evaluation unit for an inhalation dispenser, in which the air to be inhaled is sucked in through ventilation slots of the evaluation unit, and in which an internal pressure sensor is moreover provided, which is designed to detect the negative pressure that is created in the evaluation unit during aspiration of air by the user.

A problem with detecting inhalation by a user is that it is difficult to detect the airflow fully. In particular, there is the danger that a measuring device for detecting the air flow will increase the flow resistance considerably and thus be disadvantageous as regards correct inhalation by the user.

Object and Solution

The object of the invention is to make available an evaluation unit, and an inhaler together with an evaluation unit, which permit comfortable and effortless inhalation but at the same time allow the amount of air inhaled to be detected with sufficient reliability.

According to the invention, an inhaler is proposed for this purpose which, in accordance with known inhalers, has a housing with a mouthpiece and with a chamber for a container unit surrounded by a chamber wall. The chamber is designed to be open at one end, so that the container unit is insertable into the chamber at this open end.

The container unit itself has, in a generic fashion, an outlet connector, which is connected to and communicates with a discharge channel of the housing, and a container for storing the medium before discharge. An outlet valve of the container unit can be opened by moving the container relative to the outlet connector. In particular, the container can be under pressure, in order to automatically release the contained medium when the outlet valve is opened, in particular a previously isolated and defined dose of the medium. Designs having pumps with two valves, and a pump chamber arranged in between, are also known and are covered by the invention.

After insertion, the container faces toward the open end of the chamber, such that the container can be pressed down by a user in order thereby to open the outlet valve and allow medium to escape through the discharge channel to a discharge opening at the end of the discharge channel. In the non-actuated state, the container preferably protrudes out of the chamber.

The discharge is intended to take place with simultaneous inhalation by the user. An annular gap is therefore provided between the container and the chamber wall, through which annular gap air is sucked in during inhalation. As intended, this air mixes with medium flowing out of the container through the discharge opening. The mixture is inhaled by the user.

The inhaler according to the invention has an evaluation unit for evaluating the use. The evaluation unit is placed on the end of the container that points away from the outlet connector and that points toward the open end of the chamber. The evaluation unit can be pressed down together with the container. According to the invention, the evaluation unit is designed to detect the air sucked in at the mouthpiece and in particular through the annular gap and for this purpose comprises a measuring channel with a measuring channel inlet and a measuring channel outlet which forms part of a first flow path for air flowing into the open end of the chamber from an environment and which, between the measuring channel inlet and the measuring channel outlet, has a flow sensor for detecting the air flowing through the measuring channel. In addition to the first flow path through the measuring channel, there is also a second flow path for air flowing into the open end of the chamber from an environment, wherein the second flow path does not lead through the measuring channel. Instead, the second flow path leads past the measuring channel through the annular gap and/or through other openings in the housing of the inhaler.

The first flow path and the second flow path are coordinated with each other in such a way that the flow resistance of the first flow path corresponds at least to the flow resistance of the second flow path. This means that, when air is sucked in at the mouthpiece, a maximum of half of the air is passed through the measuring channel.

An inhaler according to the invention, with an evaluation unit according to the invention, is characterized in that at least half and preferably most of the air flowing into the housing from an environment and reaching the mouthpiece during inhalation is sucked in along the second flow path, which does not lead through the measuring channel. The second flow path includes the totality of the flow paths which lead from an environment to the mouthpiece by bypassing the measuring channel.

Only at most half of the air, preferably a much smaller proportion, is sucked in through the measuring channel and is therefore subjected to the comparatively high flow resistance there.

The invention is based on the knowledge that it is possible, with sufficient accuracy, to determine the total amount of air sucked in, i.e., the amount of air sucked in along the first flow path through the measuring channel and along the second flow path past the measuring channel, by solely evaluating the air flow along the first flow path. In the simplest case, there is an approximately linear relationship between the air flows. If this is not the case, the air flow in the second flow path can be calculated from the air flow through the first flow path by additional formula-based relationships or using test series stored in tables. Depending on the type of evaluation, it is not necessary to calculate the air flow through the second flow path, since the evaluation of the detected air flow of the first flow path alone is sufficient for assessment of the inhalation.

The evaluation unit, which provides the measuring channel, is designed in such a way that the evaluation unit is placed onto the end of the container of the container unit. Instead of pressing on the container floor to dispense, the user presses on the evaluation unit, which is then pressed down together with the container. The evaluation unit, which also comprises electronic components and is therefore comparatively expensive, is usually provided for repeated use with several inhalers or at least several container units, so that, after the inhaler or the container unit has been changed, the evaluation unit separated from the previous container unit is placed onto the new container unit.

The measuring channel is integrated in the evaluation unit and extends from the measuring channel inlet to the measuring channel outlet. The measuring channel inlet and the measuring channel outlet are spaced apart from each other. The measuring channel itself is circumferentially closed and contains the flow sensor, which can be designed in various ways, a thermal flow sensor being preferred. The mean cross-sectional area of the measuring channel preferably measures between 0.2 $mm^2$ and 4 $mm^2$. The narrowest cross-sectional area of the measuring channel preferably measures between 0.1 $mm^2$ and 2 $mm^2$. The length is preferably between 10 mm and 60 mm.

As has already been described, the flow resistance through the second flow path past the measuring channel corresponds at most to that of the first flow path. However, the flow resistance through the first flow path is preferably considerably higher than that of the second flow path and preferably corresponds to at least ten times the flow resistance through the second flow path, in particular preferably at least 25 times and furthermore preferably at least 35 times the flow resistance through the second flow path.

It is preferred that the flow resistance along the first flow path is at least 1,000,000 $N{\cdot}s/m^5$ and the flow resistance along the second flow path is a maximum of 1,000,000 $N{\cdot}s/m^5$. The flow resistance along the first flow path is preferably at least 5,000,000 $N{\cdot}s/m^5$. Furthermore preferably, the flow resistance along the second flow path is a maximum of 500,000 $N{\cdot}s/m^5$.

Despite the fact that this preferably given large difference in the flow resistance leads to only a small proportion of the sucked-in air flowing along the first flow path and through the measuring channel, it has been shown that, with sufficiently precise detection of the air flow through the first flow path, the total amount of air sucked in can be reliably estimated.

In order to be able to calculate the total amount of air or the total air flow with the desired precision or to permit an appropriate evaluation on the basis solely of the measured air flow, it is advantageous if the air flow flowing through the measuring channel is detected with comparative accuracy. In principle, very different sensors can be used to implement the flow sensor. For example, it is possible that an element that is deflectable counter to a restoring force is provided in the measuring channel, the deflection of which element is detected and used as a measure of the air flow. Provision can also be made, for example, that a rotor-like element is provided rotatably in the measuring channel, the rotational speed of which element is detected and used as a measure of the air flow.

However, it has been shown that the preferably only small proportion of air that is guided through the measuring channel can be determined particularly precisely and therefore particularly advantageously by a flow sensor which is designed as a thermal/calorimetric flow sensor. Such a calorimetric sensor has two temperature sensors and, arranged between them, a heating element.

The thermal flow sensor is designed to generate a heated zone in the sensor channel by the heating element and to determine the resulting temperature rise at the two temperature sensors. If no air flows through the sensor channel, the same temperature is detected at both temperature sensors on account of the identical distance to the heating element. However, if air flows through the sensor channel, the heating is asymmetrical. The greater the temperature difference, the more air flows through the sensor channel.

The measuring channel is preferably provided at least partially in a measuring channel connector through which the measuring channel extends in the longitudinal direction. The measuring channel connector extends from the evaluation unit in the direction of the chamber of the inhaler. The measuring channel preferably has a shape that tapers in the direction of an outlet opening of the measuring channel, in particular a continuously tapering shape. This makes it easier to insert the measuring channel connector into the annular gap between the container and the chamber wall. The end of the measuring channel is preferably provided at the distal end of this measuring channel connector.

The evaluation unit can be designed to be substantially rotationally symmetrical with respect to an outer contour thereof. However, a design is advantageous in which the evaluation unit has a head portion which is arranged above the container and rests on the bottom thereof, wherein an apron portion extending from the head region in an angular range of $<360^\circ$ in the direction of the chamber wall is additionally provided, which extends down the side of the container. The apron portion is preferably arranged on the outside of the measuring channel connector through which the measuring channel extends.

The apron portion can perform a variety of functions. These include the fact that the apron portion can protect the measuring channel connector by being arranged on the outside of the latter, in particular in a situation in which the evaluation unit is separated from the container unit for the purpose of exchanging the container unit.

In particular, the stated design with the apron portion is well suited for achieving locking against rotation. It is preferred that the evaluation unit and the chamber wall of the chamber are matched to each other with respect to their shapes in such a way that the evaluation unit can be placed on the container only in a defined rotational position or a defined rotational position range. It has been shown that, for a sufficiently precise calculation of the total air flow on the basis of the detected air flow along the first flow path or for the assessment of inhalation solely on the basis of the air flow along the first flow path, it is important that the first flow path is largely unchangeable in terms of a course thereof. The locking against rotation ensures that the measuring channel, in particular the measuring channel inlet and the measuring channel outlet, are always at the same location relative to the other components of the inhaler. Thus, provision can be made in particular that the measuring channel inlet and the measuring channel outlet are provided on the side of the inhaler facing away from the mouthpiece, since here the influencing of the measurement result by turbulence at the mouthpiece is minimal.

In order to achieve the locking against rotation, it is preferable in particular if the evaluation unit has the aforementioned head portion and also the apron portion extending therefrom in the direction of the chamber wall. The apron portion can have an inwardly facing shape that is adapted for form-fit engagement to a non-rotationally symmetrical outer shape of the chamber wall to provide locking against rotation. The apron portion preferably already overlaps the chamber wall when not pressed down.

Additionally or alternatively to the locking against rotation being achieved by an outer overlapping of the chamber wall by the apron portion, provision can also be made that the annular gap between the container and an inner face of the chamber wall has a non-uniform inside width and is not sufficiently dimensioned circumferentially to receive the measuring channel connector through which the measuring channel extends. Accordingly, in such a configuration, the annular gap is sufficiently large only in a defined angular range, and therefore the measuring channel connector can only be inserted here when the evaluation unit is fitted.

It is particularly advantageous if the measuring channel and/or the apron portion is arranged on the opposite side from the mouthpiece when the evaluation unit is placed on the container. This leads to more comfortable handling of the inhaler, since the apron portion does not point in the direction of the user's face while the inhaler is being used. Furthermore, this arrangement is advantageous in the manner mentioned above for avoiding turbulence in the measuring channel, the turbulence being disadvantageous for the measurement.

Furthermore, a design is preferred in which the measuring channel and in particular the measuring channel connector through which the measuring channel extends are arranged in the annular gap between the chamber wall and the container, at least when the container is pressed down. This ensures that an at least substantially reproducible proportion of the inhaled air flows through the measuring channel. Particularly preferably, the outlet opening of the measuring channel is already arranged in the annular gap when the container is not pressed down, so that the danger of the measuring channel or the measuring channel connector colliding with the chamber wall when the container is pressed down is reduced.

It is particularly preferred if the evaluation unit has a flow sensor unit which has a sensor housing with a non-linear sensor channel. This is to be understood as a sensor channel that is deflected at least once. Such a flow sensor unit can be handled quite easily when assembling the evaluation unit and in particular allows the flow sensor unit to be placed on an underside of a horizontal main board in the head portion of the evaluation unit, with part of the sensor channel running parallel to the main board, while one end or preferably both ends of the sensor channel are kinked and in particular point downward in the direction of the chamber and of the annular gap there.

The orientation of the ends of the flow sensor unit and in particular of the downstream end of the sensor channel allows a rectilinearly extending measuring channel portion, formed by the measuring channel connector, to be plugged on directly during assembly. The measuring channel connector can therefore be designed as a very simple and easily demoldable plastic part. In particular, the measuring channel connector can be an integral part of an internal component of the evaluation unit, which together with an external component forms an inner space for the protected arrangement of electronic components.

The air which flows in along the first flow path and thus crosses the measuring channel and is detected here can flow in through a gap between the evaluation unit and the chamber wall. Alternatively or additionally, however, it is also possible to provide the housing of the evaluation unit with at least one aperture through which air can flow from an environment to a measuring channel inlet. Such apertures can be advantageous because the air can flow in through the apertures without influencing the outward flow of air from the measuring channel. The measurement results of the flow sensor unit are therefore reproducible to a particularly high degree.

The at least one aperture for the inward flow of air can be provided on an upper face of a head portion of the evaluation unit. Alternatively or in addition, at least one aperture for the inward flow of air can be provided on a lateral surface of the evaluation unit, in particular on the apron portion extending in the direction of the chamber wall. Inflow openings that pass through the evaluation unit, and in particular through an outer housing component of the evaluation unit, can be advantageous since in that fewer deflections of the air flow are needed and are associated with less risk of turbulent flow. This is advantageous in terms of measurement accuracy.

The second flow path, which according to the invention has a flow resistance that at most corresponds to that of the first flow path but is preferably much lower, preferably likewise runs at least in part through an annular gap between the container and the chamber wall, although other openings in the housing of the inhaler are able to permit inward flow or air past the measuring channel. The inlet into the second flow path is preferably formed by an inflow gap which is formed on the one hand by an upper end of the chamber wall and on the other hand by a head portion of the evaluation unit.

This inflow gap preferably has an inside width of at least 1 mm, this particularly preferably applying both in the state when the container is not pressed down and in the state when it is pressed down. The inflow gap can be provided uniformly about the full circumference. However, it is advantageous if the inflow gap is interrupted by the aforementioned apron portion of the evaluation unit, although this need not mean that no air can flow in below the apron portion and reach the mouthpiece along the second flow path. However, the clear gap under the skirt portion is preferably smaller.

The inflow gap, preferably at least partially restricted by the apron portion, surrounds the container preferably at least in an angular range of 180°, preferably in an angular range of between 200° and 340°. This means that in this angular range the evaluation unit does not substantially limit the flow of air into the annular gap compared to the situation without a fitted evaluation unit, and in particular the flow resistance in this angular range is increased by a maximum of 10% by the presence of the evaluation unit.

In addition to the inhaler as a whole, the invention also relates to an evaluation unit for an inhaler for dispensing an inhalable medium. All of the above information with regard to the evaluation unit applies not only to the evaluation unit as part of an inhaler, but also to the evaluation unit according to the invention as such, which is provided for coupling to a generic inhaler. Likewise, the features of the evaluation unit that are described below are preferably also provided in the above-described evaluation unit as part of an inhaler.

An evaluation unit according to the invention is provided for use with an inhaler which, in the manner customary in particular for MDI dispensers, has a housing with a mouthpiece, and a chamber surrounded by a chamber wall, with a container unit inserted therein. As has already been described above, an annular gap is provided between a container of the container unit and the chamber wall of the chamber, through which annular gap air is sucked in during inhalation, the air mixing with the medium flowing out of the container through a discharge opening.

The evaluation unit has a fastening portion with an insertion region for inserting the bottom of the container in an insertion direction. The fastening portion is preferably designed to enter into a clamping connection with the container. For this purpose, the insertion region is preferably adapted to the outer contour and in particular the diameter of the container. Alternatively, the fastening portion can also be adjustable, in order to be placed onto containers of different dimensions. For this purpose, the evaluation unit can have an at least two-part fastening portion which delimits an insertion region, the size of the insertion region being able to be adapted by moving the two parts.

The evaluation unit according to the invention also has a measuring channel connector which extends parallel to the insertion direction and through which the measuring channel extends, through which measuring channel a proportion of the air flowing in during inhalation can pass into the annular gap, the measuring channel connector being provided to protrude into the annular gap from above.

A flow sensor is provided in the measuring channel in order to detect the air flowing through the measuring channel. As has already been described above, different types of flow sensors are possible here. The use of the thermal flow sensor already described is preferred, which has a heating element and which detects the temperature increase caused by the latter at two temperature sensors downstream and upstream of the heating element. As mentioned above, the mean cross-sectional area of the measuring channel preferably measures between 0.2 $mm^2$ and 4 $mm^2$, and the length of the measuring channel preferably measures between 10 mm and 60 mm.

As has already been described, only a proportion, preferably only a small proportion, of the air inhaled by the user flows through the measuring channel. Only this proportion is detected by the flow sensor.

The evaluation unit preferably has a control circuit which receives output signals from the flow sensor and is provided to evaluate the flow signals. The evaluation unit is designed to use the air flow along the first flow path to calculate the total air flow along the first and second flow paths. In the simplest case, the total air flow is calculated by multiplying the detected air flow by a factor determined on the basis of the flow resistances.

The evaluation unit is preferably also designed to calculate the total air flow on the basis of a non-linear relationship between the air flow in the first flow path and the total air flow. It has been shown that, depending on the geometry of the measuring channel, a calculation of the total air flow using a simple factor is not sufficient. The control circuit of the evaluation unit can therefore preferably determine the total air flow on the basis of table data stored therein or non-linear formula relationships.

The evaluation unit is preferably designed to place the summed air flow along both flow paths or the detected air flow along the first flow path in the context of further detected data. In particular, the evaluation unit can evaluate the air flow with regard to a timing with the pressing down of the container. For this purpose, the evaluation unit preferably also has at least one sensor which can detect the force applied to the evaluation unit and/or the pressing down of the evaluation unit and the container. The sensor can in particular be a button or a film acting as a force or pressure sensor, which button or film is arranged between an upper face of the evaluation unit and the container bottom, such that, when the evaluation unit and container are pressed down, the force acting here can be detected and conclusions can be drawn regarding the discharge. Alternatively, the sensor can also be provided in the form of a button or the like that detects the relative displacement of the evaluation unit with respect to the wall of the chamber, wherein the button being pressed onto an opposite surface of the wall thereby makes the discharge detectable.

The evaluation unit can evaluate whether a sufficient air flow has been inhaled by the user at the time of the discharge and whether the inhalation has been continued long enough after the discharge to ensure that the medicament, in particular the atomized liquid, has reached an intended target, in particular the lungs.

The sensor data detected by the evaluation unit, and the results data from evaluations made on the basis of the sensor data, can be used solely to be stored for later analysis or to be transmitted to a central server in order to enable third parties such as the physician to access the data. However, the evaluation unit is preferably designed to give a user visual, haptic or acoustic feedback concerning the detected or determined data, in particular by a display, status LEDs or a loudspeaker. Depending on the design, the feedback can take place during the inhalation procedure, so that the user can adapt the use directly according to the feedback. However, the feedback can also take place after the inhalation procedure, so that the user is informed of the conclusions that can be drawn from the detected data of the completed inhalation.

The evaluation unit preferably has a one-piece inner component which directly delimits an insertion region for fastening to the container and which at least in part defines the measuring channel, in particular has the measuring channel extending through the inner component. The measuring channel portion formed by the inner component preferably extends in a purely linear manner, such that the inner component can be designed as an easily demoldable plastic component. In particular, the inner component preferably forms in one piece the measuring channel continuation, which extends into the annular gap surrounding the container.

An outer housing of the evaluation unit is preferably formed by the inner component and a corresponding outer component, which together define an inner region in which various electronic components and/or sensors can be arranged. In particular, the measuring channel can also extend through the inner region. The inner component and the outer component can be connected to each other, for example by latching.

In particular, the evaluation unit can preferably have a receptacle for a battery, in particular a button cell, wherein a pull-out battery carrier is preferably provided to accommodate the battery. In particular, the battery carrier can form a locking portion by which the inner component and the outer component of the evaluation unit can be locked on to each other.

In addition to the flow sensor, which is essential to the invention, and the aforementioned sensor for detecting an actuating force exerted on the evaluation unit from above relative to the container, an evaluation unit according to the invention can also have further sensors. The further sensors include in particular a shaking sensor, usually implemented by an acceleration sensor, which is able to detect whether the user has shaken the container sufficiently before using the dispenser. Depending on the design, the further sensors can also detect other accelerations, in particular also those associated with the gripping of the dispenser by a user.

The sensors of the evaluation unit other than the flow sensor can in particular also be used in such a way that the flow sensor, which requires a comparatively large amount of energy, is only activated according to the output data from these other sensors.

The electronic components of the evaluation unit preferably also include a communication device for communicating with an external communication site, particularly preferably a wireless communication device. Communication devices of the usual standards are possible here, in particular according to a Wi-Fi standard (IEEE 802.11ax, 802.11ac, 802.11n, 802.11 g, 802.11b, 802.11), according to a Bluetooth standard (Bluetooth 1.0, 1.0B, 1.1, 1.2, 2.0, 2.0+EDR, 2.1, 2.1+EDR, 3.0, 3.0+HS, 3.0+DER, 4.0, 4.1, 4.2, 5.0, 5.1) or according to a mobile radio standard (GSM, EDGE, 3G, 4G, 5G, 6G). A power-saving Bluetooth communication device is particularly preferred, by which the evaluation unit can be coupled to a cell phone or another mobile terminal, which in turn permits the evaluation of the transmitted data and/or the forwarding of the data via the Internet.

BRIEF DESCRIPTION OF THE DRAWINGS

Further advantages and aspects of the invention will become clear from the claims and from the following description of preferred exemplary embodiments of the invention, which are explained below with reference to the figures.

DETAILED DESCRIPTION OF THE EXEMPLARY EMBODIMENTS

Figure 1:
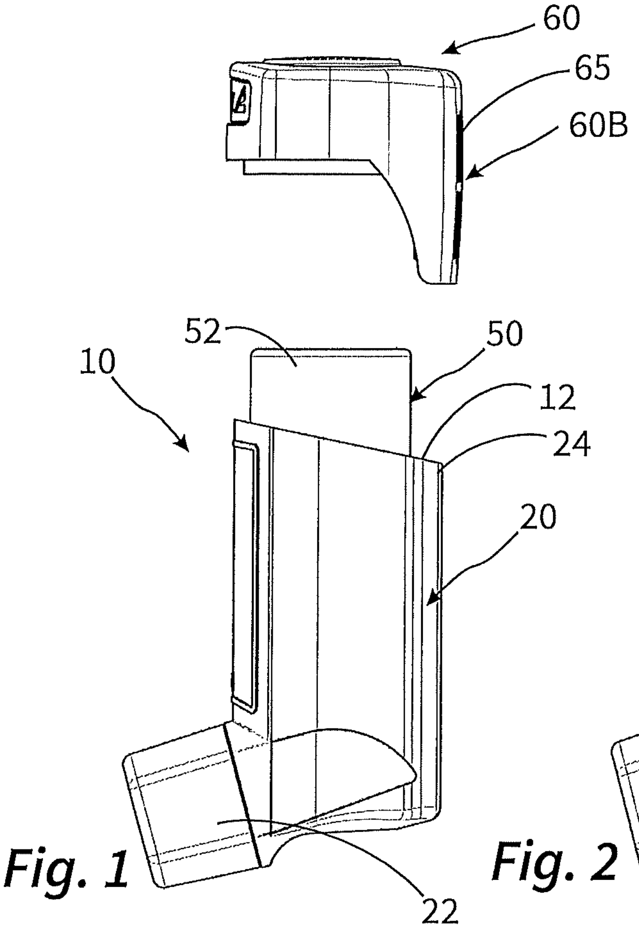
FIG. 1 shows an inhaler according to the invention, consisting of a generic inhaler and an evaluation unit according to the invention, which is not yet coupled to the generic inhaler.
Figure 2:
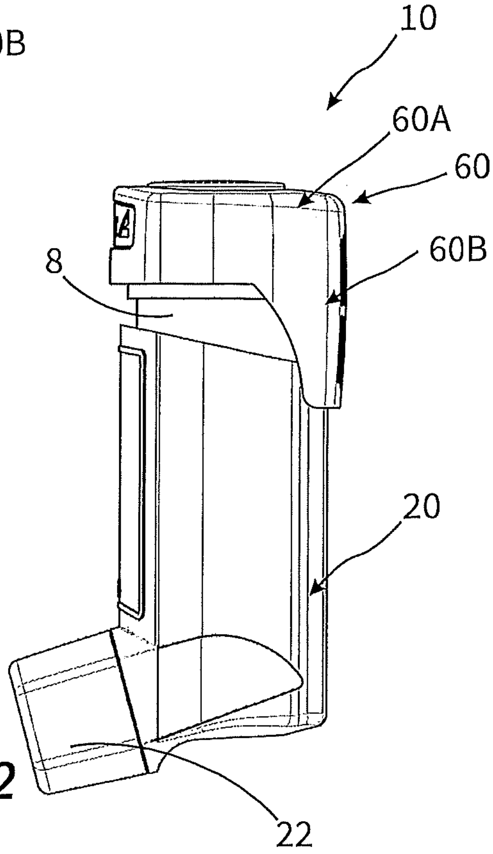
FIG. 2 shows the inhaler according to the invention with a coupled evaluation unit.
Figure 3:
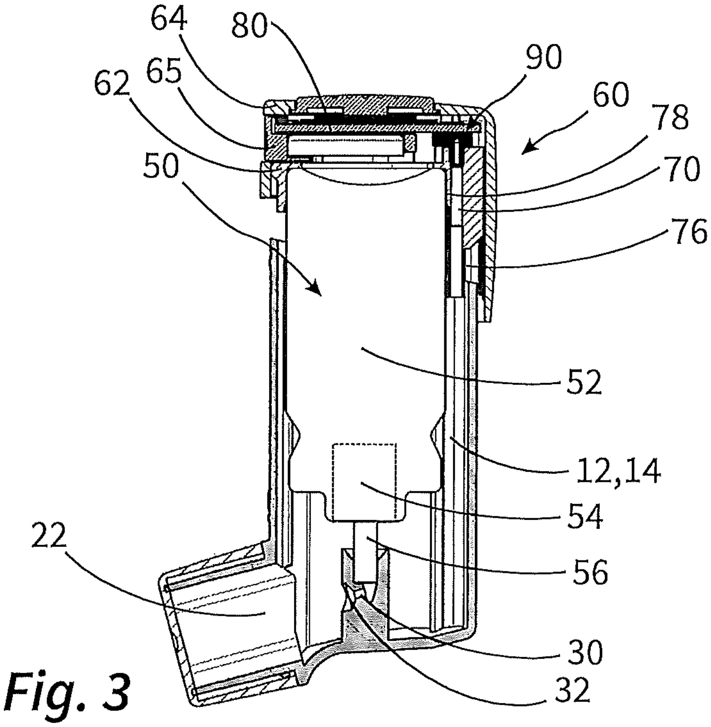
FIG. 3 shows the inhaler in a sectional view.

FIG. 1 shows an inhaler 10 according to the invention, which is composed of an essentially generic inhaler and of an evaluation unit 60 designed according to the invention. FIG. 2 shows the inhaler 10 after addition of the evaluation unit 60. FIG. 3 shows a sectional view thereof.

The essentially generic type of inhaler comprises a housing 20 which, in the manner customary for MDI dispensers, has an approximate L-shape. The housing 20 has in particular a vertical main portion, which forms a chamber 12 for a container unit 50, and also a mouthpiece 22, which is angled relative to the main portion and is shown in FIG. 1 with a protective cap attached.

The chamber 12 is delimited by a chamber wall 24 and is designed to be open at the top, such that a container unit 50 can be inserted here. Referring to FIG. 3, it can be seen that the container unit 50 has a container 52, provided for receiving liquid, and an outlet connector 56. The outlet connector 56 can be displaced in the direction of the container 52 counter to the force of a valve spring of an outlet valve 54, thereby opening the outlet valve 54. As can be seen in FIG. 3, the container unit 50 is accommodated in the chamber 12 in an upside down position. The outlet connector 56 protrudes into a receiving structure of the housing 20 which has a discharge channel 30 and a discharge opening 32 at the end of the discharge channel 30. If the container 52 is pressed down, liquid is discharged through the outlet connector 56 and the discharge channel 30 and the discharge opening 32 in the direction of the mouthpiece 22 and mixes with air that is inhaled by the user at the same time. This air is sucked into the inhaler 10 through an annular gap 14 between the container 52 and the chamber wall 24.

The evaluation unit 60, not yet attached in FIG. 1, has a head portion 60A, which in the attached state in FIGS. 2 and 3 is located predominantly above the container 52, and also an apron portion 60B protruding laterally therefrom. In a manner that will be seen from the figures that follow, the apron portion 60B is designed to correspond to the chamber wall 24, such that, in the attached state in FIGS. 2 and 3, the apron portion 60B prevents the evaluation unit 60 as a whole from being able to rotate about the main axis of the container 52. Even when the evaluation unit 60 is attached, a wide inflow gap 8 remains between the evaluation unit 60 and an upper edge of the chamber wall 24. The distance of the wide inflow gap 8 is of relevance, because the wide inflow gap 8 ensures that the user inhales air through the annular gap 14 counter to only a slight flow resistance.

As can be seen from FIG. 3 and as is explained in more detail in the illustrations that follow, the evaluation unit 60 has a measuring channel connector 76 which has a measuring channel 70 running through the measuring channel connector 76 and which protrudes into the annular gap 14 between the chamber wall 24 and the container 52. Furthermore, the evaluation unit 60 has an insertion region 78 which is adapted to the dimensions of the container 52 in such a way that the insertion region 78 enters into a clamping connection with the latter and can be released without application of great force.

FIG. 3 also shows that the evaluation unit 60 is closed off from the outside primarily by an inner component 62 and an outer component 64, which together delimit an inner region with a main board 80 and with a flow sensor unit 90 attached to the latter.

Figure 4:
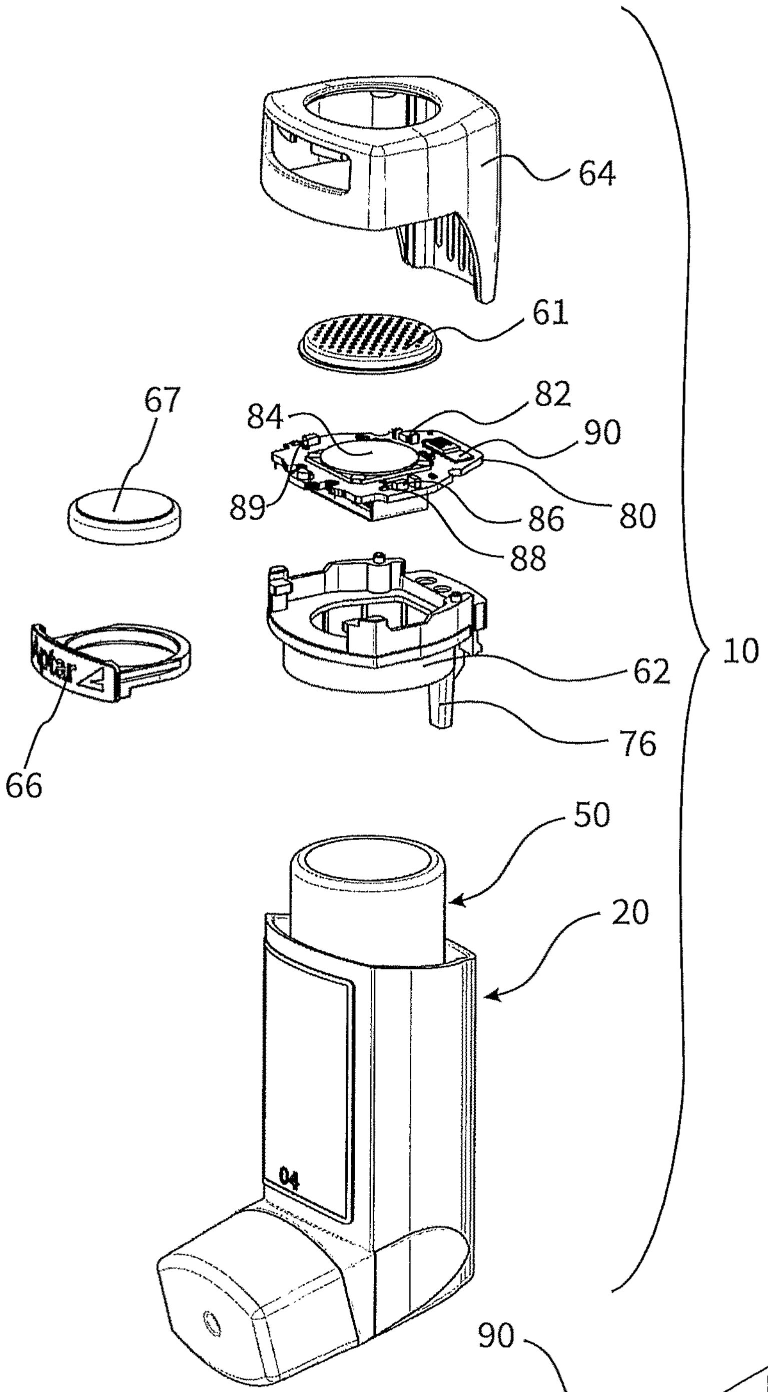
FIG. 4 shows an exploded view, from which the individual components of the evaluation unit can be seen.

The individual components of the evaluation unit 60 can be seen in particular from FIG. 4.

It will be seen in FIG. 4 that, in addition to the inner component 62 and the outer component 64, the evaluation unit 60 comprises in particular a main board 80, which is connected to the outer component 64 in a manner not shown and on an underside thereof has a receiving well for a battery 67 and the battery tray 66 of the latter. When the battery carrier 66 is inserted here, the inner component 62 and the outer component 64 are locked on to each other. Between the board 80 and the outer component 64, an actuation surface 61 is also provided, which interacts with a film 84 for force detection. This can in particular be a film whose electrical resistance undergoes a change when the film is pressed together. A processor 82, an acceleration sensor 86 and a miniaturized loudspeaker 88 and a Bluetooth communication device 89 are also attached to the board.

Figure 5:
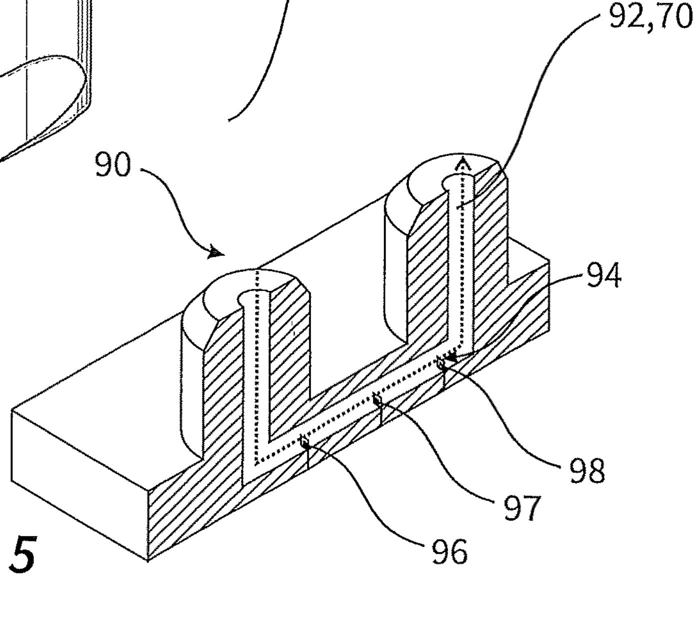
FIG. 5 shows a sectional view of a flow sensor unit of the evaluation unit.
Figure 6:
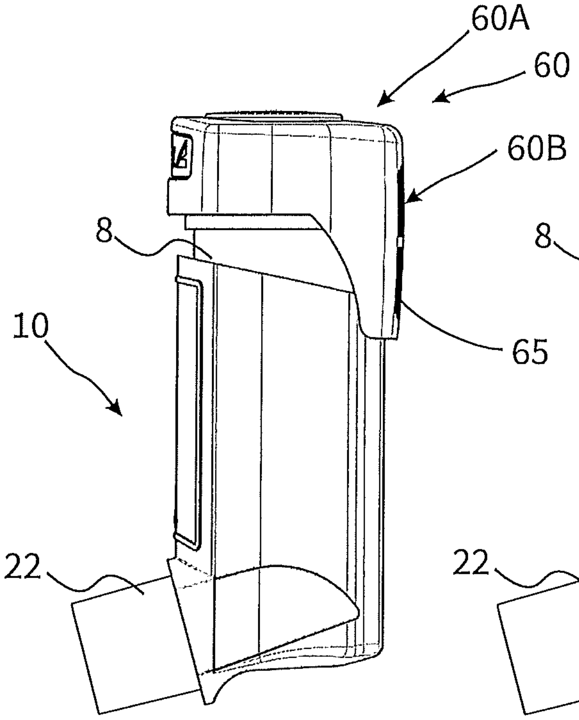
FIGS. 6 and 7 show the inhaler in use, in the not yet pressed down and in the pressed down state of the container and the evaluation unit.
Figure 7:
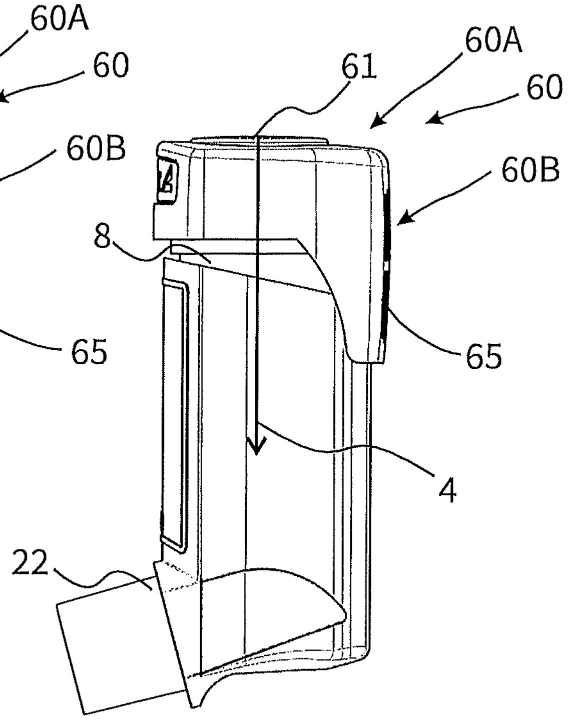

In the context of the invention, however, the most essential component on the board 80 is a flow sensor unit 90, which is mounted on the underside of the board 80 and is shown in section in FIG. 5 in a position tilted through 180°. The flow sensor unit 90 has a sensor channel 92 which is angled twice by 90° in each case and which is part of the already mentioned measuring channel 70. In the sensor channel 92, a flow sensor 94 is provided which is composed of a plurality of elements, namely of two temperature sensors 96, 98, between which a heating element 97 is arranged. If no air flows through the sensor channel 92, then heating of the heating element 97 symmetrically causes identical heating of the air at both temperature sensors. When air flows through the flow sensor unit 90 along the dotted line, the heating takes place asymmetrically. The greater the air flow, the lower the temperature at the temperature sensor 96 and the higher the temperature at the temperature sensor 98.

FIGS. 6 to 9 illustrate the use of the inhaler and the evaluation that takes place. Proceeding from the state of FIG. 6, the user holds the inhaler 10, in the orientation clearly illustrated in the figures, in front of their face and encloses the mouthpiece 22 with their lips. They then inhale air and, in the manner illustrated in FIG. 7, presses with a finger on the actuation surface 61, wherein the evaluation unit 60 as a whole, together with the container 52, is pressed down in the direction of arrow 4, and a discharge of atomized liquid through the discharge opening 32 thus takes place.

The air that has been sucked in in the meantime flows for the most part through the gap 8 into the annular gap 14 between the container 52 and the chamber wall 24. A smaller proportion of the air additionally flows through the apertures 65 in the outer component 64 into the annular gap 14.

Figure 8:
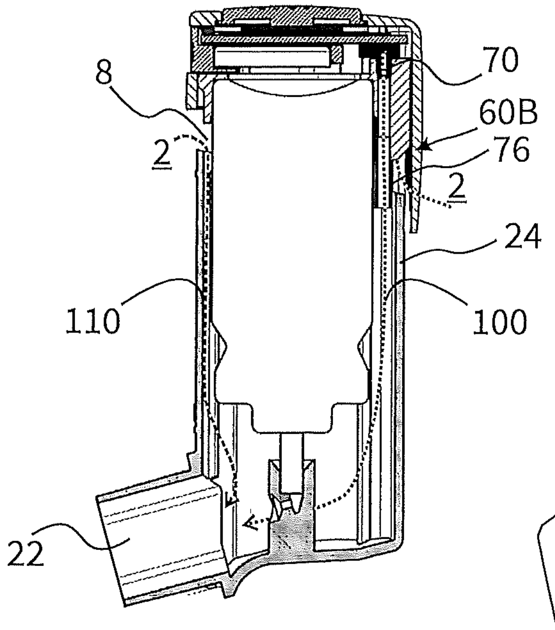
FIGS. 8 and 9 show, in different sections, the flow paths of the air during use of the inhaler.
Figure 9:
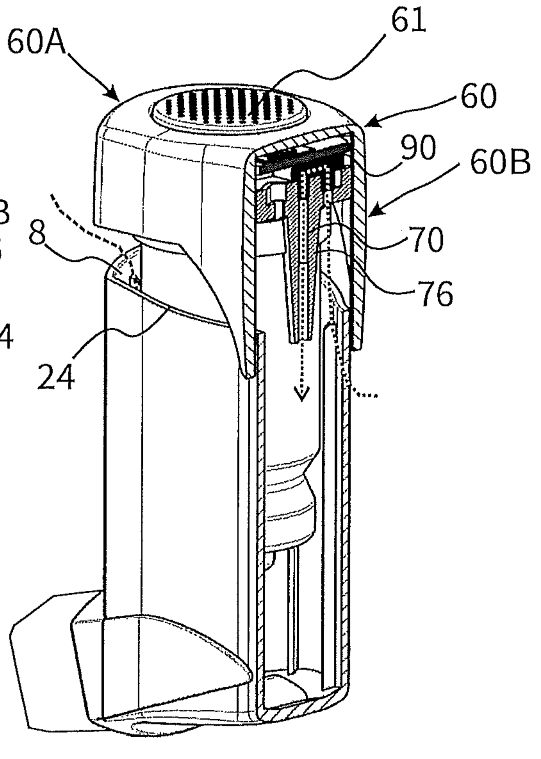

Referring to FIG. 8, it will be seen that a large part of the air flows in along the flow path 110 shown with dashed lines. Since both the inflow gap 8 and the annular gap 14 cause little flow resistance, the air flowing in on the flow path 110 flows largely unimpeded to the mouthpiece 22. At the same time, however, air also flows along a flow path 100 to the mouthpiece 22. The flow path 100 runs through the apertures 65 and an aperture of the inner component 62 into the measuring channel 70. The most essential part of this measuring channel 70 is the sensor channel 92 in the flow sensor unit 90 shown in FIG. 5. There, the air flow is measured using the flow sensor 94. The air flows onward into that part of the measuring channel 70 that runs through the measuring channel connector 76, and the air thus reaches the annular gap 14.

Although a comparatively small proportion of the total air flow of both flow paths 110, 100 is formed here by the air flowing along the flow path 100 and through the measuring channel 70, in the present case about 1% to 2% of the total air flow, it is possible, on account of a defined relationship between the air flows along the flow paths 100, 110, to draw a conclusion regarding the total air flow.

After the completion of an inhalation procedure that has been detected by the force sensor 84, it is thus possible, for example, for the processor 82 of the evaluation unit 60 to calculate whether the inhalation has taken place in the desired manner, in particular whether the user has inhaled sufficiently deeply and whether the inhalation and the triggering of the discharge were correctly timed in relation to each other. If this is the case, the loudspeaker 88 can be used to emit a suitable noise. If the discharge procedure does not take place within the desired parameters, another kind of noise can make this clear to the user.

In a manner not shown in detail, in addition to immediate notification to the user, data can also be stored or passed on, for example to a cell phone, such that the data can be evaluated at a later point in time by other people involved, for example the prescribing physician. The communication device 89 can be used for this purpose. In particular, the communication device 89 establishes a connection to a smartphone, from which the data can be forwarded. The detected data can also be supplemented with geolocation data by the inhaler itself or by the smartphone.

The different flow paths 100, 110 have the effect that a precise measurement of the inhaled air flow is possible at the same time, without having the consequence of making inhalation considerably more difficult for the user.

The invention claimed is:

1. An inhaler for dispensing an inhalable medium, the inhaler comprising:

a housing with a mouthpiece and with a chamber, the chamber being surrounded by a chamber wall and is open at one end;

a container unit arranged in the chamber;

the container unit having an outlet connector which is attached to a discharge channel of the housing in a communicating manner, and also a container for storing the medium before discharge, wherein, by moving the container with respect to the outlet connector, an outlet valve of the container unit can be opened;

the container of the container unit facing the open end of the chamber so that the container can be pressed down in order thereby to open the outlet valve and allow medium to pass through the discharge channel to a discharge opening at an end of the discharge channel;

an annular gap between the container and the chamber wall of the chamber, through which annular gap air can be sucked in during inhalation and mixed with the medium flowing out through the discharge opening;

an evaluation unit placed onto an end of the container facing away from the outlet connector and which can be pressed down together with the container, wherein the evaluation unit is designed to detect the air sucked in at the mouthpiece;

the evaluation unit comprising a measuring channel with a measuring channel inlet and a measuring channel outlet, wherein the measuring channel forms part of a first flow path for air flowing into the open end of the chamber from an environment and, between the measuring channel inlet and the measuring channel outlet, has a flow sensor for detecting the air flowing through the measuring channel; and a second flow path for air flowing into the open end of the chamber from an environment, wherein the second flow path does not lead through the measuring channel; and the first flow path and the second flow path are matched to each other in such a way that a flow resistance of the first flow path corresponds at least to a flow resistance of the second flow path;

wherein air passing through the first flow path does not come from an opening to the environment that also allows air into the second flow path.

2. The inhaler as claimed in claim 1, wherein:

the flow resistance of the first flow path from an environment to the mouthpiece measures at least 1,000,000 $N \cdot s/m^5$; and/or the flow resistance of the second flow path from an environment to the mouthpiece measures a maximum of 1,000,000 $N \cdot s/m^5$; and/or the flow resistance of the first flow path is at least a factor of 10 greater than the flow resistance of the second flow path.

3. The inhaler as claimed in claim 1, wherein:

the flow sensor comprises a thermal flow sensor having two temperature sensors and a heating element arranged between the two temperature sensors.

4. The inhaler as claimed in claim 1, wherein:

a measuring channel connector through which the measuring channel extends has a shape that tapers in a direction of an outlet opening of the measuring channel.

5. The inhaler as claimed in claim 1, wherein:

the evaluation unit has a head portion and an apron portion extending therefrom in an angular range <360° in a direction of the chamber wall, wherein the apron portion is arranged outside a measuring channel connector through which the measuring channel extends.

6. The inhaler as claimed in claim 1, wherein:

the evaluation unit and the chamber wall of the chamber are matched to each other in such a way that the evaluation unit can be placed onto the container in a defined rotational position or a defined rotational position range.

7. The inhaler as claimed in claim 6, wherein:

the evaluation unit has a head portion, and an apron portion extending therefrom in the direction of the chamber wall, wherein the apron portion has an inwardly facing shape that is adapted for form-fit engagement on a non-rotationally symmetrical outer shape of the chamber wall to provide locking against rotation; and/or the annular gap between the container and an inner face of the chamber wall has a non-uniform inside width and is not sufficiently dimensioned circumferentially to accommodate a measuring channel connector through which the measuring channel extends; and/or in the rotational position or the rotational position range in which the evaluation unit can be placed onto the container, the measuring channel is arranged opposite the mouthpiece.

8. The inhaler as claimed in claim 1, wherein:

the measuring channel outlet of the measuring channel is arranged in the annular gap at least when the container is pressed down.

9. The inhaler as claimed in claim 8, wherein the measuring channel outlet of the measuring channel is already arranged in the annular gap when the container is not pressed down.

10. The inhaler as claimed in claim 1, wherein:

the evaluation unit has a flow sensor unit which has a sensor housing with a non-linear sensor channel.

11. The inhaler as claimed in claim 10, wherein the sensor channel is bent twice, in each case by 90°.

12. The inhaler as claimed in claim 10, wherein the evaluation unit has a main board for receiving electronic components, which main board is provided orthogonally to a direction of displacement of the container in a head portion of the evaluation unit, wherein the flow sensor unit is fastened directly on the main board, and wherein an inlet of the sensor channel and/or an outlet of the sensor channel point in the direction of the annular gap.

13. The inhaler as claimed in claim 1, wherein:

a housing of the evaluation unit has at least one aperture for air to flow into the measuring channel.

14. The inhaler as claimed in claim 13, wherein:

at least one aperture allowing air to flow in is provided on an upper face of a head portion of the evaluation unit; and/or at least one aperture allowing air to flow in is provided on a lateral surface of the evaluation unit.

15. The inhaler as claimed in claim 14, wherein the at least one aperture is provided on the lateral surface of the evaluation unit in an apron portion extending in the direction of the chamber wall.

16. The inhaler as claimed in claim 1, wherein:

the second flow path runs through an inflow gap, the inflow gap being formed by an upper end of the chamber wall and by a head portion of the evaluation unit.

17. The inhaler as claimed in claim 16, wherein:

the inflow gap surrounds the container at least in an angular range of 180°; and/or the inflow gap has a width between the head portion and the upper end of the chamber wall of at least 1 mm.

18. The inhaler as claimed in claim 1, wherein:

the evaluation unit has a control circuit which receives output signals from the flow sensor and is provided to evaluate the output signals.

19. The inhaler as claimed in claim 18, wherein:

the evaluation unit is designed to use air flow along the first flow path to calculate a total air flow along the first and second flow paths, wherein the evaluation unit is also designed to calculate the total air flow on the basis of a non-linear relationship between the air flow in the first flow path and the total air flow; and/or the evaluation unit evaluates the air flow that is detected or the total air flow that is calculated with regard to a strength thereof and/or with regard to a timing thereof with the pressing down of the container; and/or the evaluation unit is designed to give a user visual, haptic or acoustic feedback, wherein the evaluation unit can be designed to give the feedback during the inhalation procedure and/or after the inhalation procedure.

20. The inhaler as claimed in claim 1, wherein:

the evaluation unit has a one-piece inner component which directly delimits an insertion region for fastening to the container and which at least in part defines the measuring channel; and/or the evaluation unit has an at least two-part fastening portion which delimits an insertion region, the size of the insertion region being adaptable by moving two parts of the at least two-part fastening portion; and/or the evaluation unit has a receptacle for a battery.

21. The inhaler as claimed in claim 20, further comprising a pull-out battery carrier to accommodate the battery, and the battery carrier forms a locking portion with which an inner component and an outer component of the evaluation unit can be locked on to each other.

22. The inhaler as claimed in claim 1, wherein:

the evaluation unit has a sensor for detecting accelerations and/or for detecting a shaking movement; and/or the evaluation unit has a sensor for detecting an actuation force, exerted on the evaluation unit from above, relative to the container; and/or the evaluation unit has an output device in the form of a display, in the form of at least one signal light and/or an acoustic signal generator; and/or the evaluation unit has a communication device for communication with an external communication site.

23. The inhaler as claimed in claim 22, wherein the sensor for detecting the actuation force is in the form of a sensor film that changes an electrical resistance thereof when compressed.

24. The inhaler as claimed in claim 22, wherein the communication device comprises a mobile terminal configured for communication according to a Wi-Fi standard, a Bluetooth standard or a mobile radio standard.

25. An evaluation unit for an inhaler for dispensing an inhalable medium, the evaluation unit being for use with an inhaler which has a housing with a mouthpiece and with a chamber which is surrounded by a chamber wall, the evaluation unit being open at one end and has a container unit inserted therein, wherein an annular gap is provided between a container of the container unit and the chamber wall of the chamber, through which annular gap air can be sucked in during inhalation and mixed with the medium flowing out of the container through a discharge opening, wherein a second flow path is provided for air flowing into the open end of the chamber from an environment, the evaluation unit comprising:

a fastening portion with an insertion region for inserting a bottom of the container in an insertion direction; and a measuring channel connector which extends parallel to the insertion direction and through which a measuring channel extends through which a proportion of the air flowing in during inhalation reaches the annular gap, wherein the measuring channel connector is provided to protrude from above into the annular gap, wherein the measuring channel forms part of a first flow path for air flowing into the open end of the chamber from an environment, and the second flow path does not lead through the measuring channel;

wherein the first flow path and the second flow path are matched to each other in such a way that a flow resistance of the first flow path corresponds at least to a flow resistance of the second flow path; and wherein the measuring channel has a flow sensor for detecting the air flowing through the measuring channel; and wherein air passing through the first flow path does not come from an opening to the environment that also allows air into the second flow path.

* * * * *